US009725456B2

(12) United States Patent
Howell et al.

(10) Patent No.: US 9,725,456 B2
(45) Date of Patent: Aug. 8, 2017

(54) QUARTERNARY AMMONIUM PERFLUOROALKOXY SALTS FOR PREPARATION OF PERFLUOROPOLYETHERS

(71) Applicants: THE CHEMOURS COMPANY FC LLC, Wilmington, DE (US); TRINITY WESTERN UNIVERSITY, Langley (CA)

(72) Inventors: Jon Lee Howell, Bear, DE (US); Chadron Mark Friesen, Langley (CA); Benson Jacob Jelier, Langley (CA)

(73) Assignees: THE CHEMOURS COMPANY FC, LLC, Wilmington, DE (US); TRINITY WESTERN UNIVERSITY, Langley (CA)

( * ) Notice: Subject to any disclaimer, the term of this patent is extended or adjusted under 35 U.S.C. 154(b) by 0 days.

(21) Appl. No.: 14/655,781

(22) PCT Filed: Jan. 10, 2014

(86) PCT No.: PCT/US2014/010984
§ 371 (c)(1),
(2) Date: Jun. 26, 2015

(87) PCT Pub. No.: WO2014/110329
PCT Pub. Date: Jul. 17, 2014

(65) Prior Publication Data
US 2015/0336968 A1     Nov. 26, 2015

Related U.S. Application Data

(60) Provisional application No. 61/751,301, filed on Jan. 11, 2013.

(51) Int. Cl.
| | |
|---|---|
| C07D 487/08 | (2006.01) |
| C10M 169/06 | (2006.01) |
| C07D 213/74 | (2006.01) |
| C07F 9/54 | (2006.01) |
| C07C 209/00 | (2006.01) |
| C07C 209/68 | (2006.01) |
| C07C 211/63 | (2006.01) |
| C07D 487/18 | (2006.01) |
| C07D 295/037 | (2006.01) |
| C07C 29/00 | (2006.01) |
| C08G 65/22 | (2006.01) |
| C08G 65/00 | (2006.01) |
| C08G 65/26 | (2006.01) |

(52) U.S. Cl.
CPC ............ *C07D 487/08* (2013.01); *C07C 29/00* (2013.01); *C07C 209/00* (2013.01); *C07C 209/68* (2013.01); *C07C 211/63* (2013.01); *C07D 213/74* (2013.01); *C07D 295/037* (2013.01); *C07D 487/18* (2013.01); *C07F 9/5407* (2013.01); *C08G 65/007* (2013.01); *C08G 65/226* (2013.01); *C08G 65/2621* (2013.01); *C08G 65/2624* (2013.01); *C10M 169/06* (2013.01)

(58) Field of Classification Search
CPC ................................................... C07D 487/01
See application file for complete search history.

(56) References Cited

U.S. PATENT DOCUMENTS

| | | | |
|---|---|---|---|
| 3,322,826 A | 5/1967 | Moore | |
| 3,449,389 A | 6/1969 | Warnell | |
| 4,657,687 A | 4/1987 | Caporiccio et al. | |
| 2002/0019483 A1 | 2/2002 | Sato et al. | |
| 2008/0139683 A1 | 6/2008 | Flynn et al. | |
| 2011/0079043 A1 | 4/2011 | Flynn et al. | |

FOREIGN PATENT DOCUMENTS

| | | |
|---|---|---|
| FR | 1373014 A1 | 3/1963 |
| GB | 1033574 | 6/1966 |

OTHER PUBLICATIONS

International Search Report, PCT/US2014/010984, Mailed Mar. 20, 2014.
Miyazaki et al., Protonation and ion exchange equilibria of weak base anion-exchange resins, Talanta, 85, 2011 1798-1804.
Cheburkov et al., Perfluoroalcohols, Journal of Fluorine Chemistry, 118, 2002, 123-126.
Chen et al, Perfluoroalkylations and perfluorooxaalkylations. Part 2. Copper-mediated cross-couling of secondary perfiuorooxaalkyl iodides and aryl halides, Journal of Fluorine Chemistry, 65, 1993, 59-65.
Kostjuk et al., Anionic Ring-Opening Polymerization of Hexafiuoropropelene Oxide using alkali Metal fluorides as catalysts: a mechanistic study, Macromolecules, 2009, 42, 612-619.
Kolomeitsev et al., Hxaalylguanidinium and 2 Dialkylamino 1,3 dimethylimidazolinium Trimethyldifluorosiliconates and Perfluoroalkoxides Accidental Isolation and molecular structure, Inorganic chemistry, 2002, 41, 6118-6124.
Kolomeitsev et al, Versatile application of trifluoromethyl triflate, Tetrahedron Letters, 59, 2008, 449-454.

*Primary Examiner* — Paul V Ward

(57) ABSTRACT

The present invention relates to anhydrous tetraalkyl pnictogen perfluoroalkoxy salts and a process to produce anhydrous tetraalkyl pnictogen perfluoroalkoxy salts. The process involves contacting a hydrofluoroether and an amine to produce a tetraalkyl pnictogen perfluoroalkoxy salt in the presence of a solvent. The present invention also relates to processes of preparing fluoroalkyl ether acid fluoride polymers using tetraalkyl pnictogen perfluoroalkoxy salt. The present invention further relates to some novel fluorinated alkyl polyether polymers.

5 Claims, No Drawings

QUARTERNARY AMMONIUM PERFLUOROALKOXY SALTS FOR PREPARATION OF PERFLUOROPOLYETHERS

FIELD OF THE INVENTION

The invention relates to a new initiator comprising quaternary ammonium perfluoroalkoxy salts. These salts are useful in the polymerization of epoxides or oxetane to form perfluoropolyethers, for example, (poly)hexafluoropropylene oxide homopolymers and oxetane polymers.

BACKGROUND OF THE INVENTION

Hereinafter trademarks or trade names are shown in upper case characters.

Perfluoropolyethers (hereinafter PFPE) are fluids having important uses in oils and greases for use under extreme conditions. The three commercial PFPEs, KRYTOX (from E.I. du Pont de Nemours and Company, Inc., Wilmington Del.), FOMBLIN and GALDEN (from, Solvay Specialty Polymers, Milan, Italy) and DEMNUM (from Daikin Industries, Osaka, Japan) differ in chemical structure. A review of KRYTOX is found in *Synthetic Lubricants and High-Performance Fluids*, Rudnick and Shubkin, Eds., Marcel Dekker, New York, N.Y., 1999 (Chapter 8, pp. 215-237). A review of FOMBLIN and GALDEN is found in *Organofluorine Chemistry*, Banks et al., Eds., Plenum, New York, N.Y., 1994, Chapter 20, pp. 431-461, and for DEMNUM, in *Organofluorine Chemistry* (op. cit.), Chapter 21, pp. 463-467.

The anionic polymerization of hexafluoropropylene epoxide as described by Moore in U.S. Pat. No. 3,322,826 can be used to produce KRYTOX fluids. The resulting poly (hexafluoropropylene epoxide) PFPE fluids are hereinafter described as poly(HFPO) fluids.

The initial polymer has a terminal acid fluoride, which is hydrolyzed to the acid followed by fluorination. The structure of a poly(HFPO) fluid is shown by Formula 1:

$$CF_3-(CF_2)_2-O-[CF/(CF_3)-CF_2-O]_s-R_f^I \quad \text{(Formula 1)}$$

wherein s is an integer from 2-100 and $R_f^I$ is $CF_2CF_3$ or $CF(CF_3)_2$, with the ratio of ethyl to isopropyl terminal group ranging from 20:1 to 50:1.

DEMNUM fluids are produced by sequential oligomerization and fluorination of 2,2,3,3-tetrafluorooxetane (tetrafluorooxetane), yielding the structure of Formula 2.

$$F-[(CF_2)_3-O]_t-R_f^{II} \quad \text{(Formula 2)}$$

wherein $R_f^{II}$ is $CF_3$ or $C_2F_5$ and t is an integer from 2-200.

A common characteristic of the PFPE fluids is the presence of perfluoropropyl initial groups and perfluoroalkyl terminal groups.

Commonly, these perfluoroalkyl ethers can be modified by reacting the acid fluoride produced from the polymerization process. There is interest for functionalized perfluorinated polyethers and difunctional perfluorinated polyethers for uses such as lubricants, additives and catalysts. New initiators are needed to control the polymerization process to produce longer chain PFPEs. These compounds can also reduce costs by allowing for a continuous polymerization process using such initiators. There also is a need for new initiator systems for polymerization of these PFPEs. The present invention meets these needs.

SUMMARY OF THE INVENTION

The first embodiment of the present invention is a process to produce anhydrous tetraalkyl pnictogen (Group 15) perfluoroalkoxy salts comprising contacting a hydrofluoroether and an amine to produce the tetraalkyl pnictogen perfluoroalkoxy salt in the presence of a solvent.

The second embodiment of the invention is a process for the preparation of a fluoroalkyl ether acid fluoride polymer comprising contacting an initiator comprising one or more anhydrous quaternary pnictogen salts with one or more monomers comprising perfluoroalkylene epoxide, perfluoroalkylene, partially fluorinated alkylene epoxide, or mixtures thereof.

The third embodiment of the invention is a composition comprising, consisting essentially of, or consisting of a fluorinated alkyl polyether polymer of formula:

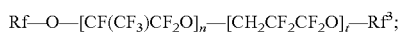

wherein $R_f$— is a linear, branched or cyclic fluoroalkyl of 7 to 10 carbons, a linear, branched or cyclic fluoroalkyl of 1 to 10 carbons substituted by —Cl, —Br or —I, non-fluorinated aryls, or non-fluorinated aryls substituted by —O—R', —Cl, —Br or —I wherein —R' is an linear, branched or cyclic alkyl of 1 to 10 carbons; n is an integer from 2 to 100, t is an integer from 2 to 200; $Rf^3$ is a linear or branched fluoroalkyl of 1 to 6 carbons.

The fourth embodiment of the invention is a composition comprising, consisting essentially of, or consisting of a tetraalkyl pnictogen salt of formula

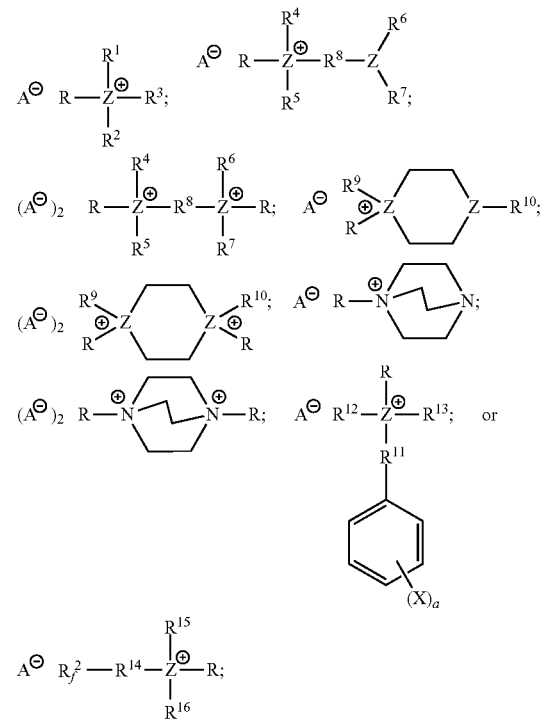

or mixtures thereof, wherein Z is N or P; each A is independently $R_f$— or $R_f$—O— wherein $R_f$— is a linear, branched or cyclic fluoroalkyl of 4 to 10 carbons optionally substituted by —Cl, —Br or —I, non-fluorinated aryls, or non-fluorinated aryls substituted by —O—R', —Cl, —Br or —I wherein —R' is an linear, branched or cyclic alkyl of 1 to 10 carbons; $R_f^2$ is a linear or branched fluoroalkyl of 1 to 10 carbons; —$R^1$, —$R^2$, —$R^3$, —$R^4$, —$R^5$, —$R^6$, —$R^7$, —$R^9$, —$R^{10}$, —$R^{12}$, —$R^{13}$, —$R^{14}$, and —$R^{15}$ are each independently a hydrogen or alkyl of 1 to 10 carbons wherein the alkyl may be linear, branched, or cyclic; —$R^8$, —$R^{11}$, and —$R^{14}$ are each independently a divalent alkyl of 1 to 10 carbons wherein the alkyl may be linear, branched, or cyclic; each X is independently a halogen; a is an integer from 0 to 5; and —R is methyl, ethyl, or propyl.

DETAILED DESCRIPTION OF THE INVENTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

This invention is directed to a process to produce anhydrous tetraalkyl pnictogen perfluoroalkoxy salts, a process for the preparation of a perfluoroalkyl ether acid fluoride polymer, novel fluorinated alkyl polyether polymers, and novel anhydrous tetraalkyl pnictogen perfluoroalkoxy salts.

A first embodiment of the present invention is a process to produce anhydrous tetraalkyl pnictogen perfluoroalkoxy salts comprising contacting a hydrofluoroether and an amine to produce the tetraalkyl pnictogen perfluoroalkoxy salt in the presence of a solvent. The process may further comprise decomposing the tetraalkyl pnictogen perfluoroalkoxy salt to produce a tetraalkyl pnictogen fluoride salt and a perfluoroalkyl acid fluoride. The process may further comprise separating the tetraalkyl pnictogen fluoride salt from the perfluoroalkyl acid fluoride. These anhydrous tetraalkyl pnictogen perfluoroalkoxy salts are useful in the polymerization of perfluoropolyalkyl ethers having longer starting groups and added functionality.

The hydrofluoroether useful in the present invention is $R_f^4$—O—R; wherein $R_f^4$ is a linear, branched or cyclic fluoroalkyl of 1 to 10 carbons optionally substituted by Cl, Br or I, non-fluorinated aryls, or non-fluorinated cyclic groups of formula —$C_nY_{2n}$ wherein each Y is independently H, O—R', Cl, Br, or I wherein —R' is an linear, branched or cyclic alkyl of 1 to 10 carbons; and —R is methyl, ethyl, or propyl. Examples include, but are not limited to: $CF_3CF_2CF_2CF_2OCH_3$, $(CF_3)_2CFCF_2OCH_3$, and $CF_3CF_2CF_2OCH_3$. These are commercially available as HFE-7100 (mixture of $CF_3CF_2CF_2CF_2OCH_3$ and $(CF_3)_2CFCF_2OCH_3$) and HFE-7000 ($CF_3CF_2CF_2OCH_3$).

The amines useful in the present invention comprise, consist essentially of, or consist of chemical compound of the following formulae:

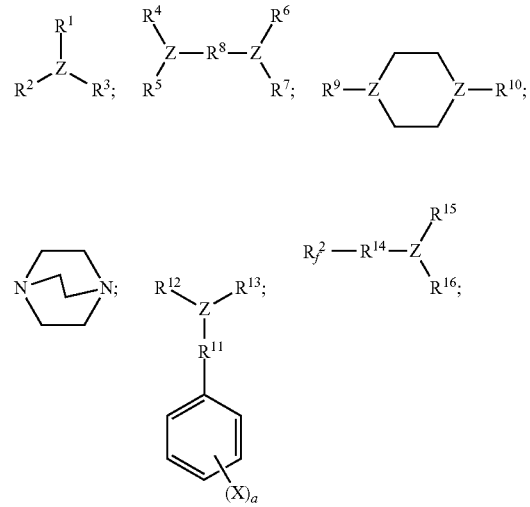

or mixtures thereof;

wherein Z is N or P; $R_f^2$ is a linear or branched fluoroalkyl of 1 to 10 carbons; —$R^1$, —$R^2$, —$R^3$, —$R^4$, —$R^5$, —$R^6$, —$R^7$, —$R^9$, —$R^{10}$, —$R^{12}$, —$R^{13}$, —$R^{14}$, and —$R^{15}$ are each independently hydrogen or alkyl of 1 to 10 carbons wherein the alkyl may be linear, branched, or cyclic; —$R^8$, —$R^{11}$, and —$R^{14}$ are each independently divalent alkyl of 1 to 10 carbons wherein the alkyl may be linear, branched, or cyclic; each X is independently a halogen; and a is an integer from 0 to 5. Examples of amines include, but are not limited to, trimethylamine, triethylamine, tripropylamine, tri(isopropyl)amine, tributylamine, 1,4-dimethylpiperazine, 1,4-diazobicyclo[2,2,2-]octane, N,N-dimethylbenzylamine, and tetramethylethylenediamine.

The process of the present invention produces quaternary pnictogen salts of the following formula:

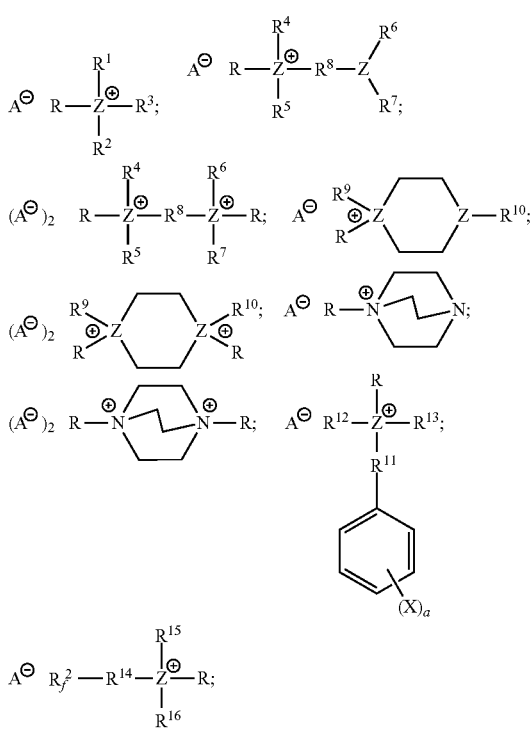

or mixtures thereof;
wherein Z is N or P; each A is independently $R_f$— or $R_f$—O— wherein $R_f$— is a linear, branched or cyclic fluoroalkyl of 4 to 10 carbons optionally substituted by —Cl, —Br or —I, non-fluorinated aryls, or non-fluorinated aryls substituted by —O—R', —Cl, —Br or —I wherein —R' is an linear, branched or cyclic alkyl of 1 to 10 carbons; $R_f^2$ is a linear or branched fluoroalkyl of 1 to 10 carbons; —$R^1$, —$R^2$, —$R^3$, —$R^4$, —$R^5$, —$R^6$, —$R^7$, —$R^9$, —$R^{10}$, —$R^{12}$, —$R^{13}$, —$R^{14}$, and —$R^{15}$ are each independently a hydrogen or alkyl of 1 to 10 carbons wherein the alkyl may be linear, branched, or cyclic; —$R^8$, —$R^{11}$, and —$R^{14}$ are each independently a divalent alkyl of 1 to 10 carbons wherein the alkyl may be linear, branched, or cyclic; each X is independently a halogen; a is an integer from 0 to 5; and —R is methyl, ethyl, or propyl.

In the present embodiment, the contacting occurs in the presence of a solvent. Any solvent can be used provided that the reactants and products are readily soluble in the solvent. Preferably, the solvent is a hydrofluoroether of formula $R_f^4$—O—R, such as defined above.

The second embodiment of the present invention is a process for the preparation of a fluoroalkyl ether acid fluoride polymer comprising contacting an initiator comprising, consisting essentially of, or consisting of one or more anhydrous quaternary pnictogen salts, as defined above, with one or more partially fluorinated monomers, fully fluorinated monomers, or mixtures thereof. In some embodiments of this invention, the one or more monomers comprise, consist essentially of, or consist of perfluoroalkylene epoxide, perfluoroalkylene, partially fluorinated alkylene epoxide, or mixtures thereof. Preferably, the perfluoroalkylene and partially fluorinated alkylene epoxide monomers are selected from the group consisting of hexafluoropropylene oxide, hexafluoropropylene, tetrafluorooxetane, and mixtures thereof.

In the present invention, contacting an initiator comprising, consisting essentially of, or consisting of one or more anhydrous quaternary pnictogen salts with one or more partially fluorinated monomers, fully fluorinated monomers, or mixtures thereof occurs in an anhydrous solvent. The anhydrous solvent can be any solvent that readily solvates the initiator, monomers and resulting polymer. Preferably, the anhydrous solvent is hydrofluoroether, hexafluoroxylene, acetonitrile, dimethyl ether, diethyl ether, tetraglyme, or mixtures thereof.

The present embodiment produces a fluoroalkyl ether acid fluoride polymer of formula:

$R_f$—O—[CF(CF$_3$)CF$_2$O]$_n$—Rf$^1$—COF.

$R_f$—O—[CH$_2$CF$_2$CF$_2$O]$_t$—Rf$^1$—COF; or $R_f$—O—([CF(CF$_3$)CF$_2$O]$_n$—[CH$_2$CF$_2$CF$_2$O]$_t$—Rf$^1$—COF;

wherein $R_f$— is a linear, branched or cyclic fluoroalkyl of 1 to 10 carbons, a linear, branched or cyclic fluoroalkyl of 1 to 10 carbons substituted by —Cl, —Br, or I, non-fluorinated aryls, or non-fluorinated aryls substituted by —O—R', —Cl, —Br, or —I wherein —R' is an linear, branched or cyclic alkyl of 1 to 10 carbons; n is an integer from 2 to 100, t is an integer from 2 to 200; Rf$^1$ is a divalent linear or branched fluoroalkyl of 1 to 6 carbons.

The length and composition of each $R_f$— group is dependent on the quaternary pnictogen salts used during the polymerization. It is known that polymerization of fluorinated and partially fluorinated monomers with metal fluorides, such as cesium fluoride, results in a starting group of the polymer commensurate with the monomer used. That is to say that by polymerizing the hexafluoropropylene oxide with cesium fluoride results in a CF$_3$CF$_2$CF$_2$O— starting group of the polymer. It is surprising that by polymerizing the monomers with quaternary pnictogen salts as defined above, the polymerization produces a mixture of polymers having starting group $R_f$ (from the anion of the quaternary pnictogen salt) as defined above as well as having starting group CF$_3$CF$_2$CF$_2$O— as produced in the traditional polymerization processes. For example, polymerizations of hexafluoropropylene oxide with a quaternary pnictogen salt of formula CF$_3$CF$_2$CF$_2$CF$_2$O$^-$N(CH$_3$)$_4$$^+$ will produce a mixture of fluoroalkyl ether acid fluoride polymers of formula CF$_3$CF$_2$CF$_2$O—[CF(CF$_3$)CF$_2$O]$_n$—Rf$^1$—COF and CF$_3$CF$_2$CF$_2$CF$_2$O—[CF(CF$_3$)CF$_2$O]$_n$—Rf$^1$—COF.

Likewise, if the hexafluoropropylene oxide was polymerized using a quaternary pnictogen salt of formula BrCF$_2$CF$_2$CF$_2$CF$_2$O$^-$N(CH$_3$)$_4$$^+$, the polymer product is a mixture of fluoroalkyl ether acid fluoride polymers of formula CF$_3$CF$_2$CF$_2$O—[CF(CF$_3$)CF$_2$O]$_n$—Rf$^1$—COF and BrCF$_2$CF$_2$CF$_2$CF$_2$O—[CF(CF$_3$)CF$_2$O]$_n$—Rf$^1$—COF.

Another example of the present invention, is that polymerizing hexafluoropropylene oxide using a quaternary pnictogen salt of formula

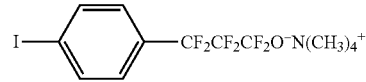

produces a mixture of fluoroalkyl ether acid fluoride polymers of formula

CF$_3$CF$_2$CF$_2$O—[CF(CF$_3$)CF$_2$O]$_n$—Rf$^1$—COF and

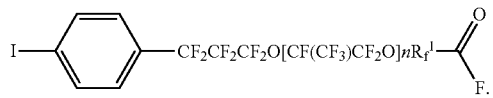

This added functionality is very useful in various applications such as thermally stable additives.

The third embodiment of the present invention is a composition comprising, consisting essentially of, or consisting of a fluorinated alkyl polyether polymer of formula:

R$_f$—O—[CF(CF$_3$)CF$_2$O]$_n$—Rf$^3$;

R$_f$—O—[CF$_2$CF$_2$CF$_2$O]$_t$—Rf$^3$; or

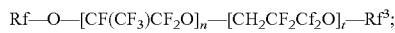

Rf—O—[CF(CF$_3$)CF$_2$O]$_n$—[CH$_2$CF$_2$Cf$_2$O]$_t$—Rf$^3$;

wherein R$_f$— is a linear, branched or cyclic fluoroalkyl of 7 to 10 carbons, a linear, branched or cyclic fluoroalkyl of 1 to 10 carbons substituted by —Cl, —Br or —I, non-fluorinated aryls, or non-fluorinated aryls substituted by —O—R', —Cl, —Br or —I wherein —R' is an linear, branched or cyclic alkyl of 1 to 10 carbons; n is an integer from 2 to 100, t is an integer from 2 to 200; Rf$^3$ is a linear or branched fluoroalkyl of 1 to 6 carbons.

These fluorinated alkyl polyether polymers are prepared by contacting an initiator comprising, consisting essentially of, or consisting of quaternary pnictogen salts, as defined above, with partially fluorinated, fully fluorinated monomers, or mixtures thereof to produce a fluoroalkyl ether acid fluoride polymer. These fluoroalkyl ether acid fluoride polymer are then hydrolyzed and fluorinated to produce polymers of the following formula:

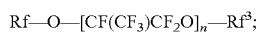

Rf—O—[CF(CF$_3$)CF$_2$O]$_n$—Rf$^3$;

Rf—O—[CF$_2$CF$_2$CF$_2$O]$_t$—Rf$^3$; or

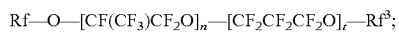

Rf—O—[CF(CF$_3$)CF$_2$O]$_n$—[CF$_2$CF$_2$CF$_2$O]$_t$—Rf$^3$;

wherein R$_f$—, n, t, and Rf$^3$ are as defined above.

These polymers are useful as high performance lubricating oils. These oils can be thickened to produce greases. The oils can be thickened with a thickener and said perfluoropolyether is present in said composition in the range of from about 0.1 to about 50 weight % based on said composition. Thickeners are selected from the group consisting of poly(tetrafluoroethylene), fumed silica, boron nitride, and combinations of two or more thereof.

The fourth embodiment of the present invention is a composition comprising, consisting essentially of, or consisting of a tetraalkyl pnictogen salt of formula:

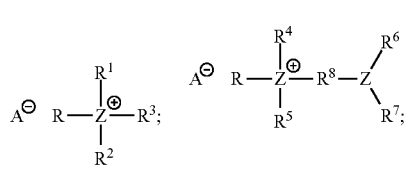

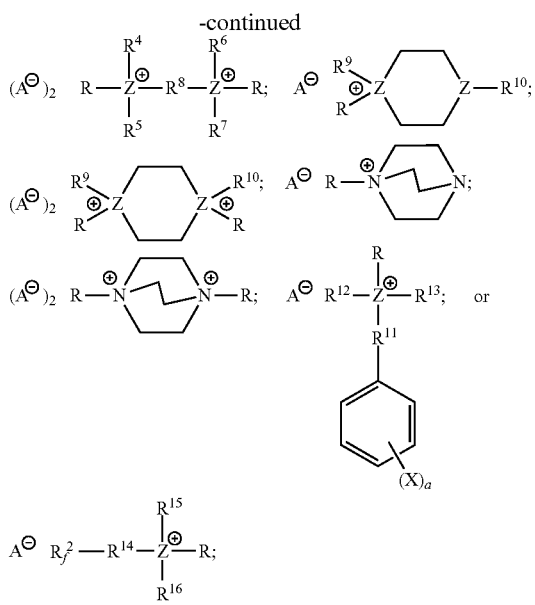

or mixtures thereof,
wherein Z is N or P; each A is independently R$_f$— or R$_f$—O— wherein R$_f$— is a linear, branched or cyclic fluoroalkyl of 1 to 10 carbons optionally substituted by —Cl, —Br or —I, non-fluorinated aryls, or non-fluorinated aryls substituted by —O—R', —Cl, —Br or —I wherein —R' is an linear, branched or cyclic alkyl of 1 to 10 carbons; R$_f^2$ is a linear or branched fluoroalkyl of 1 to 10 carbons; —R$^1$, —R$^2$, —R$^3$, —R$^4$, —R$^5$, —R$^6$, —R$^7$, —R$^9$, —R$^{10}$, —R$^{12}$, —R$^{13}$, —R$^{14}$, and —R$^{15}$ are each independently a hydrogen or alkyl of 1 to 10 carbons wherein the alkyl may be linear, branched, or cyclic; —R$^8$, —R$^{11}$, and —R$^{14}$ are each independently a divalent alkyl of 1 to 10 carbons wherein the alkyl may be linear, branched, or cyclic; each X is independently a halogen; a is an integer from 0 to 5; and —R is methyl, ethyl, or propyl.

According to the fifth embodiment of the invention, a grease or lubricant composition is provided. Greases containing the perfluoropolyether disclosed in the third embodiment of the invention can be produced by combining the perfluoropolyether with a thickener. Examples of such thickeners include, but are not limited to, standard thickeners such as, for example, poly(tetrafluoroethylene), fumed silica, and boron nitride, and combinations of two or more thereof. The thickeners can be present in any appropriate particle shapes and sizes as known to one skilled in the art.

According to the invention, the perfluoropolyether of the invention can be present in the composition in the range of from about 0.1 to about 50, preferably 0.2 to 40, percent by weight based on the composition. The composition can be produced by any methods known to one skilled in the art such as, for example, by blending the perfluoropolyether with the thickener.

EXAMPLES

The concepts described herein will be further described in the following examples, which do not limit the scope of the invention described in the claims.

TEST METHOD AND RESULTS

Examples 1 to 21, anhydrous tetraalkyl pnictogen perfluoroalkoxy salts were prepared by reacting the corresponding hydrofluoroether and the corresponding commercially available amine or phosphine to produce the tetraalkyl pnictogen perfluoroalkoxy salt of the present invention. This reaction reported here is a novel process. Examples 1 through 11 were prepared using $CF_3CF_2CF_2OCH_3$ (commercially available from 3M as HFE-7000) as the hydrofluoroether and as the solvent. Examples 12 to 21 were prepared using a mixture of $CF_3CF_2CF_2CF_2OCH_3$ and $(CF_3)_2CFCF_2OCH_3$ (commercially available from 3M as HFE-7100) as the hydrofluoroether and as the solvent. The hydrofluoroethers and amines were first rigorously dried and degassed prior to the reactions to render anhydrous. In a typical reaction, under a nitrogen atmosphere, 0.6 mol of the respective tertiary amine and 5 mol equivalent hydrofluoroether were combined and sealed in a glass vial. The vials were heated for a period of 48 hrs. Reactions with trimethylamine were performed by vacuum transfer technique of the amine to a glass reactor capable of elevated pressure. Upon addition of the amine, the reaction tube was slowly warmed to the appropriate temperature. After 48 hours, volatiles were removed under reduced pressure affording the isolated product. Once complete, excess reagents were removed in vacuo and the perfluoroalkoxide was collected in a fine fitted disk in a glovebox and washed with 3×3 mL of anhydrous hexanes and further dried in vacuo. Trimethylamine, triethylamine, n-tripropylamine, n-tributylamine, N,N,-tetramethylethylenediamine, N,N-dimethylbenzylamine, N-methylmorpholine, 1,4-dimethylpiperzine, 1,4-diazobicyclo[2,2,2]octane, 4-dimethylaminopyridine and trimethylphosphine were used as the amine in Examples 1 to 11, respectively. Trimethylamine, triethylamine, n-tripropylamine, n-tributylamine, N, N,-tetramethylethylenediamine, N,N-dimethylbenzylamine, N-methylmorpholine, 1,4-dimethylpiperzine, 1,4-diazobicyclo[2,2,2]octane and 4-dimethylaminopyridine were used as the amine in Examples 12 to 21, respectively.

TABLE 1

Examples 1 to 21: Compositions of the tetraalkyl pnictogen salts.

| Example | Tetraalkyl Pnictogen Cation | Perfluoroalkoxide |
| --- | --- | --- |
| 1 | $N(CH_3)_4^+$ | $CF_3CF_2CF_2O-$ |
| 2 | $N(CH_2CH_3)_3CH_3^+$ | $CF_3CF_2CF_2O-$ |
| 3 | $N(CH_2CH_2CH_3)_3CH_3^+$ | $CF_3CF_2CF_2O-$ |
| 4 | $N(CH_2CH_2CH_2CH_3)_3CH_3^+$ | $CF_3CF_2CF_2O-$ |
| 5 | (N-benzyl dimethyl ammonium) | $CF_3CF_2CF_2O-$ |
| 6 | (N-methyl morpholinium) | $CF_3CF_2CF_2O-$ |
| 7 | (N,N,N',N'-tetramethyl ethylenediammonium) | $CF_3CF_2CF_2O-$ |
| 8 | (1,4-dimethyl piperazinium) | $CF_3CF_2CF_2O-$ |
| 9 | (1-methyl DABCO) | $CF_3CF_2CF_2O-$ |
| 10 | (4-dimethylamino-1-methylpyridinium) | $CF_3CF_2CF_2O-$ |
| 11 | $P(CH_3)_4^+$ | $CF_3CF_2CF_2O-$ |
| 12 | $N(CH_3)_4^+$ | $CF_3CF_2CF_2CF_2O-/(CF_3)_2CFCF_2O^-$ |
| 13 | $N(CH_2CH_3)_3CH_3^+$ | $CF_3CF_2CF_2CF_2O-/(CF_3)_2CFCF_2O^-$ |
| 14 | $N(CH_2CH_2CH_3)_3CH_3^+$ | $CF_3CF_2CF_2CF_2O-/(CF_3)_2CFCF_2O^-$ |
| 15 | $N(CH_2CH_2CH_2CH_3)_3CH_3^+$ | $CF_3CF_2CF_2CF_2O-/(CF_3)_2CFCF_2O^-$ |
| 16 | (N-benzyl dimethyl ammonium) | $CF_3CF_2CF_2CF_2O-/(CF_3)_2CFCF_2O^-$ |
| 17 | (N-methyl morpholinium) | $CF_3CF_2CF_2CF_2O-/(CF_3)_2CFCF_2O^-$ |
| 18 | (N,N,N',N'-tetramethyl ethylenediammonium) | $CF_3CF_2CF_2CF_2O-/(CF_3)_2CFCF_2O^-$ |
| 19 | (1,4-dimethyl piperazinium) | $CF_3CF_2CF_2CF_2O-/(CF_3)_2CFCF_2O^-$ |
| 20 | (1-methyl DABCO) | $CF_3CF_2CF_2CF_2O-/(CF_3)_2CFCF_2O^-$ |

TABLE 1-continued

Examples 1 to 21: Compositions of the tetraalkyl pnictogen salts.

| Example | Tetraalkyl Pnictogen Cation | Perfluoroalkoxide |
|---|---|---|
| 21 | 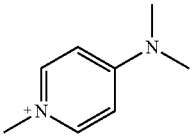 | $CF_3CF_2CF_2CF_2O^-/$ $(CF_3)_2CFCF_2O^-$ |

The following examples are provided to illustrate the characterization of tetraalkyl pnictogen salts of the present invention (Table 1), but are not intended to limit the scope thereof.

Example 1

Tetramethylammonium Heptafluoropropoxide $^1$H NMR (400 MHz, $CD_3CN$) δ3.160 (s, 3H). $^{19}$F NMR (376 MHz, $CD_3CN$) δ−125.84 ($CF_2$, s, 2F), −81.89 ($CF_3$, s, 3F), −27.67 ($CF_2O$, broad, s, 2F). Anal. Calcd. for $C_7H_{12}F_7NO$: C, 32.44; H, 4.67; N, 5.40. Found: C, 32.68; H, 5.21; N, 5.77.

Example 2

N,N-diethyl-N-methylethanaminium Heptafluoropropoxide $^1$H NMR (400 MHz, $CD_3CN$) δ1.27 (tt, $^3J_{HH}$=7.3 Hz, 2.0, 9H), 2.890 (s, 3H), 3.28 (q, $^3J_{HH}$=7.3 Hz, 6H). $^{19}$F NMR (376 MHz, $CD_3CN$) δ−125.75 ($CF_2$, s, 2F), −81.91 ($CF_3$, s, 3F), −27.92 ($CF_2O$, broad, s, 2F). Anal. Calcd. for $C_{10}H_{18}F_7NO$: C, 39.87; H, 6.02; N, 4.65. Found: C, 39.96; H, 5.48; N, 4.74.

Example 3

N-methyl-N,N-dipropylpropan-1-aminium Perfluoropropoxide $^1$H NMR (400 MHz, $CD_3CN$) δ1.07 (t, $^3J_{HH}$=7.3 Hz, 9H), 1.64-1.94 (m, 6H), 3.03 (s, 3H), 3.11-3.40 (m, 6H). $^{19}$F NMR (376 MHz, $CD_3CN$) δ−125.75 ($CF_2$, s, 2F), −81.89 ($CF_3$, s, 3F), −27.64 ($CF_2O$, broad, s, 2F). Anal. Calcd. for $C_{13}H_{24}F_7NO$: C, 45.48; H, 7.05; N, 4.08. Found: C, 45.67; H, 6.86; N, 4.12.

Example 4

N,N-dibutyl-N-methylbutan-1-aminium Perfluoropropoxide $^1$H NMR (400 MHz, $CD_3CN$) δ0.99 (t, $^3J_{HH}$=7.4 Hz, 9H), 1.37 (m, $^3J_{HH}$=7.4 Hz, 6H), 1.56-1.82 (m, 6H), 2.94 (s, 3H), 3.06-3.32 (m, 6H). $^{19}$F NMR (376 MHz, $CD_3CN$) δ−125.74 ($CF_2O$, s, 2F), −81.89 ($CF_3$, s, 3F), −27.64 ($CF_2O$, broad, s, 2F). Anal. Calc. for $C_{16}H_{30}F_7NO$: C, 49.86; H, 7.85; N, 3.63. Found: C, 49.67; H, 7.86; N, 3.83.

Example 5

N,N,N-trimethyl-1-phenylmethanaminium Perfluoropropoxide $^1$H NMR (400 MHz, $CD_3CN$) δ3.07 (s, 9H), 4.54 (s, 2H), 7.07-7.73 (m, 5H). $^{19}$F NMR (376 MHz, $CD_3CN$) δ−125.292 ($CF_2$, s, 2F), −81.081 ($CF_3$, s, 3F), −27.071 ($CF_2$, broad, s, 2F). Anal. Calc. for $C_{13}H_{16}F_7NO$: C, 46.57; H, 4.81; N, 4.18. Found: C, 46.87; H, 4.99; N, 4.32.

Example 6

4,4-dimethylmorpholin-4-ium Perfluoropropoxide $^1$H NMR (400 MHz, $CD_3CN$) δ3.19 (s, 6H), 3.41 (m, 4H), 3.94 (m, 4H). $^{19}$F NMR (376 MHz, $CD_3CN$) δ−125.834 ($CF_2$, s, 2F), −81.920 ($CF_3$, s, 3F), −27.873 ($CF_2O$, broad, s, 2F). Anal. Calcd. for $C_9H_{14}F_7NO_2$: C, 35.89; H, 4.69; N, 4.65. Found: C, 36.30; H, 4.19; N, 4.73.

Example 7

2-(dimethylamino)-N,N,N-trimethylethan-1-aminium Perfluoropropoxide $^1$H NMR (400 MHz, $CD_3CN$) δ2.24 (s, 6H), 2.64-2.73 (m, 2H), 3.16 (s, 9H), 3.39-3.47 (m, 2H), $^{19}$F NMR (376 MHz, $CD_3CN$) δ−125.772 ($CF_2$, s, 2F), −81.847 ($CF_3$, s, 3F), −27.688 ($CF_2O$, broad, s, 2F). Anal. Calcd. for $C_{10}H_{19}F_7N_2O$: C, 37.98; H, 6.06; N, 8.86. Found: C, 37.68; H, 6.57; N, 8.96.

Example 8

1,1,4-trimethylpiperazin-1-ium Perfluoropropoxide $^1$H NMR (400 MHz, $CD_3CN$) δ2.335 (s, 3H), 2.688 (broad s, 4H), 3.125 (s, 6H), 3.409 (t, $^3J_{HH}$=5.182 Hz, 4H). $^{19}$F NMR (376 MHz, $CD_3CN$) δ−125.782 ($CF_2$, s, 2F), −81.860 ($CF_3$, s, 3F), −27.686 ($CF_2O$, broad, s, 2F). Anal. Calcd. for $C_{10}H_{17}F_7N_2O$: C, 38.22; H, 5.45; N, 8.91. Found: C, 38.57; H, 5.25; N, 9.11.

Example 9

1-methyl-1,4-diazabicyclo[2.2.2]octan-1-ium Perfluoropropoxide $^1$H NMR (400 MHz, $CD_3CN$) δ2.97 (s, 3H), 3.11 (t, $^3J_{HH}$=7.54 Hz, 6H), 3.27 (t, $^3J_{HH}$=7.543 Hz, 6H). $^{19}$F NMR (376 MHz, $CD_3CN$) δ−125.786 ($CF_2$, s, 2F), −81.886 ($CF_3$, s, 3F), −27.846 ($CF_2O$, broad, s, 2F). Anal. Calcd. for $C_{10}H_{15}F_7N_2O$: C, 38.47; H, 4.84; N, 8.97. Found: C, 38.53; H, 4.40; N, 9.10.

Example 10

4-(dimethylamino)-1-methylpyridin-1-ium Perfluoropropoxide $^1$H NMR (400 MHz, $CD_3CN$) δ3.181 (s, 6H), 3.905 (s, 3H), 6.88 (d, $^3J_{HH}$=7.7 Hz, 2H), 8.03 (d, $^3J_{HH}$=7.5 Hz, 2H). $^{19}$F NMR (376 MHz, $CD_3CN$) δ−125.725 ($CF_2$, s, 2F), −81.842 ($CF_3$, s, 3F), −27.760 ($CF_2O$, broad, s, 2F). Anal. Calcd. for $C_{11}H_{13}F_7N_2O$: C, 41.00; H, 4.07; N, 8.69. Found: C, 41.40; H, 4.09; N, 8.83.

Example 11

Tetramethylphosphonium Perfluoropropoxide $^1$H NMR (400 MHz, CD$_3$CN) δ1.96 (d, $^2J_{HP}$=14.9 Hz, 12H). $^1$H{$^{31}$P} NMR (400 MHz, CD$_3$CN) δ1.96 (s, 12H). $^{19}$F NMR (376 MHz, CD$_3$CN) δ−125.792 (CF$_2$, s, 2F), −81.895 (CF$_3$, s, 3F), −27.625 CF$_2$O, broad, s, 2F). $^{31}$P {$^1$H} NMR (162 MHz, CD$_3$CN) δ24.361 (s, 1P). $^{31}$P NMR (162 MHz, CD$_3$CN) δ24.372 (m, $^2J_{PH}$=14.894). $^{13}$C NMR (101 MHz, CD$_3$CN) δ9.46 (P—CH$_3$, d, $^1J_{CP}$=56.4 Hz, 1C) (fluorinated carbons not detectable). Anal. Calcd. for C$_7$H$_{12}$F$_7$OP: C, 30.45; H, 4.38; N, 0.00 Found: C, 30.35; H, 3.89; N, <0.3.

Example 12

Tetramethylammonium n- and Iso-Nonafluorobutoxide $^1$H NMR (400 MHz, CD$_3$CN) δ3.137 (s, 3H). $^{19}$F NMR (376 MHz, CD$_3$CN) δ−26.99 (OCF$_2$, broad s, 2F), −81.64 (CF$_3$, t, $^3J_{FF}$=9.1 Hz, 3F), −122.55 (CF$_3$CF$_2$, q, $^3J_{FF}$=8.8 Hz, 2F), −126.60 (CF$_2$CF$_2$CF$_2$, s, 2F) and −18.54 (OCF$_2$, broad s, 2F), −73.69 (CF$_3$, d, $^3J_{FF}$=5.8 Hz, 6F), −180.40 (CF, s, 1F). Anal. Calcd. for C$_8$H$_{12}$F$_9$NO: C, 31.08; H, 3.91; N, 4.53. Found: C, 31.40; H, 4.14; N, 4.94.

Example 13

N,N-diethyl-N-methylethanaminium n- and Iso-Nonafluorobutoxide $^1$H NMR (400 MHz, CD$_3$CN) δ1.41 (tt, $^3J_{HH}$=7.3, 2.0 Hz, 9H), 3.02 (s, 3H), 3.41 (q, $^3J_{HH}$=7.3 Hz, 6H). $^{19}$F NMR (376 MHz, CD$_3$CN) δ−26.88 (OCF$_2$, broad s, 2F), −81.62 (CF$_3$, t, $^3J_{FF}$=9.2 Hz, 3F), −122.49 (CF$_3$CF$_2$, q, $^3J_{FF}$=9.0 Hz, 2F), −126.61 (CF$_2$CF$_2$CF$_2$, s, 2F) and −18.46 (OCF$_2$, broad s, 2F), −73.73 (CF$_3$, d, $^3J_{FF}$=6.1 Hz, 6F), −180.33 (CF, s, 1F). Anal. Calcd. for C$_{11}$H$_{18}$F$_9$NO: C, 37.61; H, 5.17; N, 3.99. Found: C, 37.97; H, 5.51; N, 4.19.

Example 14

N-methyl-N,N-dipropylpropan-1-Aminium n- and Iso-Nonafluorobutoxide $^1$H NMR (400 MHz, CD$_3$CN) δ1.11 (t, $^3J_{HH}$=7.3 Hz, 9H), 1.86 (m, 6H), 3.08 (s, 3H), 3.39 (m, 6H). $^{19}$F NMR (376 MHz, CD$_3$CN) δ−26.81 (OCF$_2$, m, 2F), −81.62 (CF$_3$, t, $^3J_{FF}$=9.0 Hz, 3F), −122.48 (CF$_3$CF$_2$, m, $^3J_{FF}$=9.5 Hz, 2F), −126.60 (CF$_2$CF$_2$CF$_2$, t, $^3J_{FF}$=8.3 Hz, 2F) and −18.39 (−OCF$_2$, m, $^3J_{FF}$=10.7 Hz, 2F), −73.71 (CF$_3$, dt, $^3J_{FF}$=10.9, $^4J_{FF}$=6.2 Hz, 6F), −180.31 (CF, m, 1F). Anal. Calcd. for C$_{14}$H$_{24}$F$_9$NO: C, 42.75; H, 6.15; N, 3.56. Found: C, 42.93; H, 6.02; N, 3.72.

Example 15

N,N-dibutyl-N-methylbutan-1-aminium n- or Iso-Nonafluorobutoxide $^1$H NMR (400 MHz, CD$_3$CN) δ0.99 (m, $^3J_{HH}$=7.4 Hz, 9H), 1.38 (m, $^3J_{HH}$=7.4 Hz, 6H), 1.66 (m, 6H), 2.93 (s, 3H), 3.17 (m, 6H). $^{19}$F NMR (376 MHz, CD$_3$CN) δ26.81 (OCF$_2$, m, 2F), −81.61 (CF$_3$, t, $^3J_{FF}$=9.1 Hz, 3F), −122.47 (CF$_3$CF$_2$, q, $^3J_{FF}$=9.1 Hz, 2F), −126.59 (CF$_2$CF$_2$CF$_2$, broad s, 2F) and −18.30 (—OCF$_2$, broad s, 2F), −73.71 (CF$_3$, d, $^3J_{FF}$=5.9, 6F), −180.31 (CF, m, 1F). Anal. Calcd. for C$_{17}$H$_{30}$F$_9$NO: C, 46.89; H, 6.95; N, 3.22. Found: C, 47.24; H, 7.19; N, 3.31.

Example 16

N,N,N-trimethyl-1-phenylmethanaminium n- and Iso-Nonafluorobutoxide $^1$H NMR (400 MHz, CD$_3$CN) δ3.086 (s, 9H), 4.564 (s, 2H), 7.559 (m, 4.5H). $^{19}$F NMR (376 MHz, CD$_3$CN) δ−26.93 (OCF$_2$, m, 2F), −81.59 (CF$_3$, tt, $^3J_{FF}$=13.6, $^4J_{FF}$=2.8 Hz, 3F), −122.51 (CF$_3$CF$_2$, m, $^3J_{FF}$=9.5 Hz, 2F), −126.55 (CF$_2$CF$_2$CF$_2$, t, $^3J_{FF}$=8.4 Hz, 2F) and −18.44 (OCF$_2$, dm, $^3J_{FF}$=20.6, $^4J_{FF}$=10.9 Hz, 2F), −73.69 (CF$_3$, dt, $^3J_{FF}$=11.0, $^4J_{FF}$=6.1 Hz, 6F) −180.363 (CF, m, 1F). Anal. Calcd. for C$_{14}$H$_{16}$F$_9$N: C, 43.65; H, 4.19; N, 3.64. Found: C, 44.04; H, 3.73; N, 3.79.

Example 17

4,4-dimethylmorpholin-4-ium n- and Iso-Nonafluorobutoxide $^1$H NMR (400 MHz, CD$_3$CN) δ3.196 (s, 6H), 3.41 (t, $^3J_{HH}$=5.0 Hz, 4H), 3.939 (m, 4H). $^{19}$F NMR (376 MHz, CD$_3$CN) δ−27.08 (OCF$_2$, broad s, 2F), −81.63 (CF$_3$, t, $^3J_{FF}$=9.1 Hz, 3F), −122.55 (CF$_3$CF$_2$, q, $^3J_{FF}$=7.8 Hz, 2F), −126.59 (CF$_2$CF$_2$CF$_2$, t, $^3J_{FF}$=7.8 Hz, 2F) and −18.61 (OCF$_2$, m, $^3J_{FF}$=10.3 Hz, 2F), −73.73 (CF$_3$, broad d, $^3J_{FF}$=5.9 Hz, 6F), −180.40 (CF, m, 1F). Anal. Calcd. for C$_{10}$H$_{14}$F$_9$NO$_2$: C, 34.20; H, 4.02; N, 3.99. Found: C, 34.42; H, 3.55; N, 4.15.

Example 18

2-(dimethylamino)-N,N,N-trimethylethan-1-aminium n- and Iso-Nonafluorobutoxide $^1$H NMR (400 MHz, CD$_3$CN) δ2.246 (s, 6H), 2.689 (m, 2H), 3.149 (s, 9H), 3.397 (t, $^3J_{HH}$=11.96 Hz 2H). $^{19}$F NMR (376 MHz, CD$_3$CN) δ−26.91 (OCF$_2$, broad s, 2F), −81.62 (CF$_3$, t, $^3J_{FF}$=9.1 Hz, 3F), −122.51 (CF$_3$CF$_2$, q, $^3J_{FF}$=8.6 Hz, 2F), −126.58 (CF$_2$CF$_2$CF$_2$, s, 2F) and −18.46 (OCF$_2$, broad s, 2F), −73.71 (CF$_3$, broad d, $^3J_{FF}$=5.7 Hz, 6F), −180.37 (CF, m, 1F). Anal. Calcd. for C$_{11}$H$_{19}$F$_9$N$_2$O: C, 36.07; H, 5.23; N, 7.65. Found: C, 36.41; H, 5.58; N, 7.94.

Example 19

1,1,4-trimethylpiperazin-1-ium n- and Iso-Nonafluorobutoxide $^1$H NMR (400 MHz, CD$_3$CN) δ2.337 (s, 3H), 2.688 (broad s, 4H), 3.124 (s, 6H), 3.41 (t, $^3J_{HH}$=5.2 Hz, 4H). $^{19}$F NMR (376 MHz, CD$_3$CN) δ−26.89 (OCF$_2$, broad s, 2F), −81.61 (CF$_3$, t, $^3J_{FF}$=9.1 Hz, 3F), −122.50 (CF$_3$CF$_2$, q, $^3J_{FF}$=9.0 Hz, 2F), −126.57 (CF$_2$CF$_2$CF$_2$, broad s, 2F) and −18.44 (OCF$_2$, m, $^3J_{FF}$=10.2 Hz, 2F), −73.69 (CF$_3$, broad d, $^3J_{FF}$=5.9 Hz, 6F), −180.35 (CF, broad m, 1F). Anal. Calcd. for C$_{11}$H$_{17}$F$_9$N$_2$O: C, 36.27; H, 4.70; N, 7.69. Found: C, 36.68; H, 4.90; N, 7.78.

Example 20

1-methyl-1,4-diazabicyclo[2.2.2]octan-1-ium n- and Iso-Nonafluorobutoxide $^1$H NMR (400 MHz, CD$_3$CN) δ2.973 (s, 3H), 3.11 (t, $^3J_{HH}$=7.5 Hz, 6H), 3.27 (t, $^3J_{HH}$=7.5 Hz, 6H). $^{19}$F NMR (376

MHz, CD$_3$CN) δ–26.90 (OCF$_2$, broad s, 2F), –81.62 (CF$_3$, t, $^3J_{FF}$=9.1 Hz, 3F), –122.51 (CF$_3$CF$_2$, q, $^3J_{FF}$=9.1 Hz, 2F), –126.58 (CF$_2$CF$_2$CF$_2$, s, 2F) and –18.45 (OCF$_2$, broad s, 2F), –73.72 (CF$_3$, d, $^3J_{FF}$=6.1 Hz, 6F), –180.36 (CF, broad m, 1F). Anal. Calcd. for C$_{11}$H$_{15}$F$_9$N$_2$O: C, 36.47; H, 4.17; N, 7.73. Found: C, 36.90; H, 4.26; N, 8.14.

Example 21

N,N,N-trimethylpyridin-4-aminium n- and Iso-Nonafluorobutoxide $^1$H NMR (400 MHz, CD$_3$CN) δ3.312 (s, 6H), 4.026 (s, 3H), 7.00 (d, $^3J_{HH}$=7.7 Hz, 2H), 8.12 (d, $^3J_{HH}$=7.6 Hz, 2H). $^{19}$F NMR (376 MHz, CD$_3$CN) δ–26.95 (OCF$_2$, broad s, 2F), –81.62 (CF$_3$, t, $^3J_{FF}$=9.0 Hz, 3F), –122.47 (CF$_3$CF$_2$, broad s, 2F), –126.57 (CF$_2$CF$_2$CF$_2$, s, 2F) and –18.54 (OCF$_2$, broad s, 2F), –73.69 (CF$_3$, broad s, 6F), –180.31 (CF, broad m, 1F). Anal. Calcd. for C$_{12}$H$_{13}$F$_9$N$_2$O: C, 38.72; H, 3.52; N, 7.53. Found: C, 38.54; H, 3.93; N, 7.86.

Examples A to N

Following are examples that demonstrate the utility of the compounds of the invention although, it is to be understood that there is no intent to limit the invention to the precise constructions herein disclosed. Examples A to N were prepared by polymerizing hexafluoropropylene oxide and hexafluoropropylene monomers in the presence of quaternary pnictogen initiator compounds of the present invention, as polymerization imitators.

Polymerizations were carried out in a 250 mL glass round-bottomed flask equipped with inlet and outlet valves, dry ice condenser, and a mechanical stirrer. After pre-conditioning the reactor by heating 4 hours at 180° C., the reactor was cooled to room temperature and charged with solvent and initiator (as defined in Table 2 below) under a nitrogen atmosphere. The reactor was subsequently cooled in an external bath to the temperature as defined below in Table 2 with dry ice/acetonitrile under positive nitrogen pressure. While maintaining a temperature ±2° C., hexafluoropropene (HFP) was transferred to the system. Hexafluoropropylene oxide (HFPO) was then slowly introduced into the reactor with vigorous stirring over a 5 hr period. The reactor was then warmed to room temperature and the product was isolated under a nitrogen atmosphere and placed in clean, dry plastic bottles. Samples were treated with methanol to convert the acid fluoride end group to a methyl ester end group for analysis.

For Example M and the comparative example N, which were performed at room temperature and hence at elevated pressure, a different setup was required. In this case, 0.25 mmol of initiator (either Example 5 or CsF) was added to a 60 mL glass vessel capable of elevated pressure in which 4 mL of HFX and 0.05 mL tetraglyme was added and then sealed. HFPO was then fed to the reactor at 1 second intervals every 15 minutes for a period of 6 hours. In Example M, this amounted to 11 g of HFPO whereas in Example N, the total HFPO consumed was 22 g. The monomer conversion was determined gravimetrically while molecular weight distribution was determined by GC/MS, $^{19}$F NMR and/or MALDI-TOF-MS of the methyl ester derivative.

TABLE 2

Polymerization initiators, solvents, and temperature using tetraalkyl pnictogen salts of the present invention.

| Example | Initiator | Solvent | Temp (° C.) |
|---|---|---|---|
| A | N(CH$_3$)$_4$$^+$ CF$_3$CF$_2$CF$_2$CF$_2$O—/ (CF$_3$)$_2$CFCF$_2$O$^-$ | HFX/ACN/HFE-7100 | 0 |
| B | N(CH$_3$)$_4$$^+$ CF$_3$CF$_2$CF$_2$CF$_2$O—/ (CF$_3$)$_2$CFCF$_2$O$^-$ | HFX/ACN/HFE-7100 | –25 |
| C | N(CH$_3$)$_4$$^+$ CF$_3$CF$_2$CF$_2$CF$_2$O—/ (CF$_3$)$_2$CFCF$_2$O$^-$ | HFX/ACN/HFE-7100 | –30 |
| D | 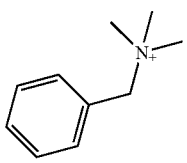 CF$_3$CF$_2$CF$_2$O— | HFX/ACN/Dimethyl Ether | –45 |
| E | N(CH$_3$)$_4$$^+$ CF$_3$CF$_2$CF$_2$CF$_2$O—/ (CF$_3$)$_2$CFCF$_2$O$^-$ | HFX/Tetraglyme | 0 |
| F | N(CH$_3$)$_4$$^+$ CF$_3$CF$_2$CF$_2$CF$_2$O—/ (CF$_3$)$_2$CFCF$_2$O$^-$ | HFX/ACN/HFE-7100 | –5 |
| G | N(CH$_3$)$_4$$^+$ CF$_3$CF$_2$CF$_2$CF$_2$O—/ (CF$_3$)$_2$CFCF$_2$O$^-$ | Tetraglyme | –30 |
| H | 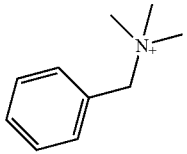 CF$_3$CF$_2$CF$_2$CF$_2$O—/ (CF$_3$)$_2$CFCF$_2$O$^-$ | Tetraglyme | –30 |
| I | N(CH$_2$CH$_3$)$_3$CH$_3$$^+$ CF$_3$CF$_2$CF$_2$CF$_2$O—/ (CF$_3$)$_2$CFCF$_2$O$^-$ | Tetraglyme | –30 |
| J | N(CH$_2$CH$_2$CH$_3$)$_3$CH$_3$$^+$ CF$_3$CF$_2$CF$_2$CF$_2$O—/ (CF$_3$)$_2$CFCF$_2$O$^-$ | Tetraglyme | –30 |
| K | N(CH$_3$)$_4$$^+$ CF$_3$CF$_2$CF$_2$O— | Tetraglyme | –30 |
| L | CsF | Tetraglyme | –30 |
| M | 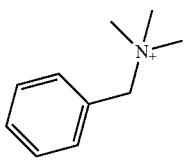 CF$_3$CF$_2$CF$_2$O— | HFX/Tetraglyme | 25 |
| N | CsF | HFX/Tetraglyme | 25 |

*HFX is hexafluoroxylene
*ACN is acetonitrile

TABLE 3

Degree of polymerization results using tetraalkyl pnictogen salts of the present invention

| | $C_3F_7O\text{—}[CF(CF_3)CF_2O]_n\text{—}Rf$ | | | $C_4F_9O\text{—}[CF(CF_3)CF_2O]_n\text{—}Rf$ | | |
|---|---|---|---|---|---|---|
| Example | Average repeat unit (n) | Degree of Polymerization (Range of n) for $C_3F_7O$ initial group | % Composition for polymers with $C_3F_7O$ initial group | Average repeat unit (n) | Degree of Polymerization (Range of n) for $C_4F_9O$ initial group | % Composition for polymers with $C_4F_9O$ initial group |
| Example L | 3.85 | 0-10 | 100 | 0 | 0 | 0 |
| Example K | 1.99 | 0-4 | 100 | 0 | 0 | 0 |
| Example M | 1.98 | 0-6 | 100 | 0 | 0 | 0 |
| Example N | 2.94 | 0-7 | 100 | 0 | 0 | 0 |
| Example G | 0.79 | 0-2 | 85 | 0.6 | 0-1 | 15 |
| Example I | 1.93 | 1-4 | 93 | 2.2 | 1-3 | 7 |
| Example J | 1.87 | 0-4 | 93 | 2.0 | 1-3 | 7 |
| Example H | 1.64 | 0-4 | 91 | 2.06 | 1-3 | 9 |

As is evidenced in Table 3, the current invention provides a new methodology to prepare oligomeric poly(HFPO) with clear advantages over existing art. Depending on the initiator, a range of functionalized materials can be prepared in a fashion more suitable for subsequent derivatization or for temperature stability applications. For instance, in a comparative Example L (Table 3) using known experimental conditions demonstrates the oligio(HFPO) with solely a perfluoropropoxy initial group whereas, with the said initiators, provide routes for the preparation of a perfluorobutoxy oligomeric HFPO (Example G up to 15%). This technology also has the particular advantage of being able to quantify the amount of chain transfer occurring within the polymerization of hexafluoropropylene oxide, an advantage that cannot be obtained with the traditional CsF/tetraglyme system under identical conditions (Comparative Example L). Surprisingly, these results obtained by GC-MS or MALDI-TOF-MS show that chain transfer is a very active process within the polymerization of hexafluoropropylene oxide even with organic based pnictogen cations under said conditions. However, as obvious to a person skilled in the art, the choice of solvent, temperature and specific nature of the corresponding cation significantly affect the degree and composition of the polymerization product. In addition, Examples M and N demonstrate that this invention is amenable to the preparation of oligio(HFPO) at ambient conditions. As disclosed here, a much larger range of conditions can be utilized for the polymerization of hexafluoropropylene oxide since the said initiators have much different and more tunable properties than prior art which was restricted to a metal alkali fluoride/glyme based system. However, the conditions represented here were chosen to demonstrate a comparison with existing processes, conditions that have been optimized for a CsF catalyst, but clearly can be tuned to afford the desired degree of polymerization and composition in a more true living polymerization model.

What is claimed is:

1. A process to produce anhydrous tetraalkyl pnictogen perfluoroalkoxy salts comprising contacting a hydrofluoroether and an amine wherein the amine is

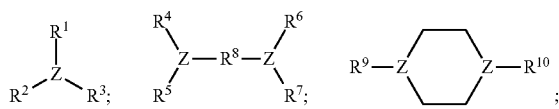

-continued

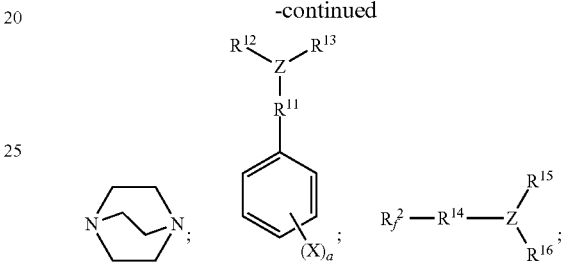

or mixtures thereof;

wherein Z is N or P; Rf2 is a linear or branched fluoroalkyl of 1 to 10 carbons; —R1, —R2, —R3, —R4, —R5, —R6, —R7, —R9, —R10, —R12, —R13, —R14, and —R15 are each independently hydrogen or alkyl of 1 to 10 carbons wherein the alkyl may be linear, branched, or cyclic; —R8, —R11, and —R14 are each independently divalent alkyl of 1 to 10 carbons wherein the alkyl may be linear, branched, or cyclic; each X is independently a halogen; and a is an integer from 0 to 5, to produce the tetraalkyl pnictogen perfluoroalkoxy salt in the presence of a solvent.

2. A process of claim 1, further comprising decomposing the tetraalkyl pnictogen perfluoroalkoxy salt to produce a tetraalkyl pnictogen fluoride salt and a perfluoroalkyl acid fluoride.

3. A process of claim 2, further comprising separating the tetraalkyl pnictogen fluoride salt from the perfluoroalkyl acid fluoride and the solvent.

4. A process of claim 1, wherein the hydrofluoroether is R—O—R wherein R is a linear, branched or cyclic fluoroalkyl of 1 to 10 carbons optionally substituted by Cl, Br or I, non-fluorinated aryls, or non-fluorinated cyclic groups of formula —$C_nY_{2n}$ wherein each Y is independently H, O—R', Cl, Br or I wherein —R' is an linear, branched or cyclic alkyl of 1 to 10 carbons; and —R is methyl, ethyl, or propyl.

5. A process of claim 1, wherein the solvent is a hydrofluoroether.

* * * * *

UNITED STATES PATENT AND TRADEMARK OFFICE
CERTIFICATE OF CORRECTION

PATENT NO. : 9,725,456 B2
APPLICATION NO. : 14/655781
DATED : August 8, 2017
INVENTOR(S) : Jon Lee Howell, Chadron Mark Friesen and Benson Jacob Jelier It is certified that error appears in the above-identified patent and that said Letters Patent is hereby corrected as shown below:

In the Title

In Column 1, Line 1, "QUARTERNARY AMMONIUM..." should read "QUATERNARY AMMONIUM...."

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*